(12) United States Patent
Irwin

(10) Patent No.: US 6,277,066 B1
(45) Date of Patent: Aug. 21, 2001

(54) ENDOCAVITY IMAGING SENSOR POSITIONING APPARATUS AND METHOD

(75) Inventor: Terry Irwin, North Liberty, IA (US)

(73) Assignee: CIVCO Medical Instruments Inc., Kalona, IA (US)

( * ) Notice: Subject to any disclaimer, the term of this patent is extended or adjusted under 35 U.S.C. 154(b) by 0 days.

(21) Appl. No.: 09/303,786

(22) Filed: Apr. 30, 1999

(51) Int. Cl.[7] .......................................................... A61B 1/00
(52) U.S. Cl. ........................ 600/115; 600/116; 600/121; 600/124
(58) Field of Search ................................... 600/115, 116, 600/121, 124, 156, 158, 470, 459

(56) References Cited

U.S. PATENT DOCUMENTS

| | | | |
|---|---|---|---|
| 4,224,929 | * | 9/1980 | Furihata .................................. 128/5 |
| 4,603,701 | * | 8/1986 | Chen ................................... 128/660 |
| 5,105,800 | * | 4/1992 | Takahashi et al. ........................ 128/4 |
| 5,331,947 | * | 7/1994 | Shturman ................................ 126/4 |
| 5,634,464 | * | 6/1997 | Jang et al. ........................ 128/660.03 |

* cited by examiner

Primary Examiner—Linda C. M. Dvorak
Assistant Examiner—Jocelyn Ram
(74) Attorney, Agent, or Firm—Merchant & Gould P.C.

(57) ABSTRACT

A directionally expandable standoff device for use with an imaging instrument is disclosed. The standoff device has an elastic sheath configured for placement over a probe of an imaging instrument and a substantially rigid cover configured for placement over the elastic sheath, the cover containing an opening exposing a portion of the elastic sheath. The standoff device allows controlled positioning of the tissue surface within the cavity of a patient's body during imaging analysis.

19 Claims, 4 Drawing Sheets

ENDOCAVITY IMAGING SENSOR POSITIONING APPARATUS AND METHOD

FIELD OF THE INVENTION

The present invention relates to a device for positioning a medical imaging instrument. More particularly, the invention is directed to an apparatus and method for controlling the distance of an imaging sensor from the tissue surface within a cavity of a patient.

BACKGROUND

Imaging instruments, such as ultrasound probes, have revolutionized the manner in which many important medical procedures are performed. These medical instruments utilize substantially non-invasive imaging techniques to explore and assess the condition of human tissue. As a result of these non-invasive imaging techniques, diagnostic and therapeutic protocols have been developed that allow many highly successful and safe procedures to be performed with a minimum of disturbance to patients.

Ultrasound and other imaging techniques have received widespread acceptance as useful diagnostic tools. The ultrasound image is created by emission of very high frequency sound waves from a transducer scanning the subject area. The sound waves are reflected back to the transducer, and corresponding data is transmitted to a processing device. The processing device analyzes the data and composes a picture for display on a monitoring screen. Ultrasound probes, and other imaging instruments, may be used in this manner for a variety of purposes, such as identifying the existence, location, and size of tumors, as well as the existence of other medical conditions, including the atrophy or hypertrophy of bodily organs.

Most ultrasound sensors perform best in resolving tissue within a particular area of its scan path and at a particular distance from the imaging probe. For example, an optimal area for image resolution may be 1 or more inches away from the image sensor surface. As a result, tissue very near the image sensor surface may not be viewable to an extent desired by the operating physician.

Increasingly, imaging instruments have been used to explore cavities of humans and animals in order to conduct routine examinations, as well as to identify evidence of illness. These endocavities, such as those associated with the human digestive and reproductive tracts, can be the location of benign and malignant tumors. Using ultrasound, these tumors can be located and assessed. However, because ultrasound probes usually perform best at a point distant from the subject tissue, endocavities can be difficult to properly examine because it can be difficult to move the probe closer or farther away from a target that is adjacent to the probe. This is an especially significant issue when examining thin tissue, such as the walls of the colon. If the thin tissue is not placed in the proper position, satisfactory imaging results are difficult to obtain.

To remedy the problem of tissue positioning, a standoff device can be placed between the image sensor and the patient's tissue to move the image sensor away from the desired scan area, placing the tissue in an optimal scanning window. Unfortunately, existing standoff devices are difficult to use, uncomfortable for patients, and do not provide adequate flexibility and control over the standoff position. Therefore, a need exists for an improved standoff device.

SUMMARY OF THE INVENTION

The present invention is directed to a directionally expandable standoff device for use with an imaging instrument In certain embodiments the standoff device includes an elastic sheath configured for placement over a probe of an imaging instrument. The standoff device also includes a substantially rigid cover configured for placement over the elastic sheath, the cover containing an opening exposing a portion of the elastic sheath. The exposed portion of the elastic sheath is configured to expand through the opening in the cover upon insertion of a fluid into the elastic sheath. This expansion of the elastic sheath moves tissue proximate the sheath, and allows precise placement of the tissue during imaging analysis. The expansion of the elastic sheath also allows for slight movement of tissue masses in order to adjust their position within the imaging field of the imaging instrument.

In certain embodiments, the exposed portion of the elastic sheath is configured and arranged such that it has an unexpanded state substantially flush with the cover of the standoff device. The exposed portion of the elastic sheath is confined to an arc of less than or equal to 180 degrees around the center of the imaging probe in certain embodiments, and to an arc of less than or equal to 90 degrees around the imaging probe in other embodiments.

In certain implementations of the invention the opening in the cover is between approximately 0.5 and 5.0 inches long, and between 0.5 and 1.5 inches wide. The standoff device may also include a conduit in fluid communication with the elastic sheath, the conduit configured and arranged to provide fluid to expand the exposed portion of the elastic sheath.

The invention is also directed to a method of examining a patient using an imaging instrument. The method includes providing an imaging instrument and a directionally expandable standoff device. The standoff device includes an elastic sheath configured for placement over the probe of an imaging instrument and a substantially rigid cover configured for placement over the expandable sheath, the cover containing an opening exposing a portion of the elastic sheath. The standoff device is expanded so as to properly position the imaging instrument relative to tissue of a patient, thereby improving imaging results.

The above summary of the present invention is not intended to describe each discussed embodiment of the present invention. This is the purpose of the figures and the detailed description which follow.

BRIEF DESCRIPTION OF THE DRAWINGS

Other aspects and advantages of the invention will become apparent upon reading the following detailed description and references to the drawings, in which.

While the invention is susceptible to various modifications and alternative forms, specifics thereof have been shown by way of example and drawings, and will be described in detail. It should be understood, however, that the intention is not to limit the invention to particular embodiments described. On the contrary, the intention is to cover modifications, equivalents, and alternatives falling within the spirit and scope of the invention as defined by the appended claims.

DETAILED DESCRIPTION

The present invention is directed to an expandable standoff device for use with an imaging instrument. In certain embodiments the standoff device includes an elastic sheath configured for placement over a probe of an imaging instrument. The standoff device also includes a substantially rigid cover configured for placement over the elastic sheath. The cover contains an opening exposing a portion of the elastic sheath. The exposed portion of the elastic sheath is configured to expand through the opening in the cover upon insertion of a fluid into the elastic sheath. This expansion of the elastic sheath allows precise placement of the surface of the tissue within an endocavity of a patient's body, and also allows for slight movement of tissue masses in order to adjust their position within the imaging field of the imaging instrument.

Figure 1:
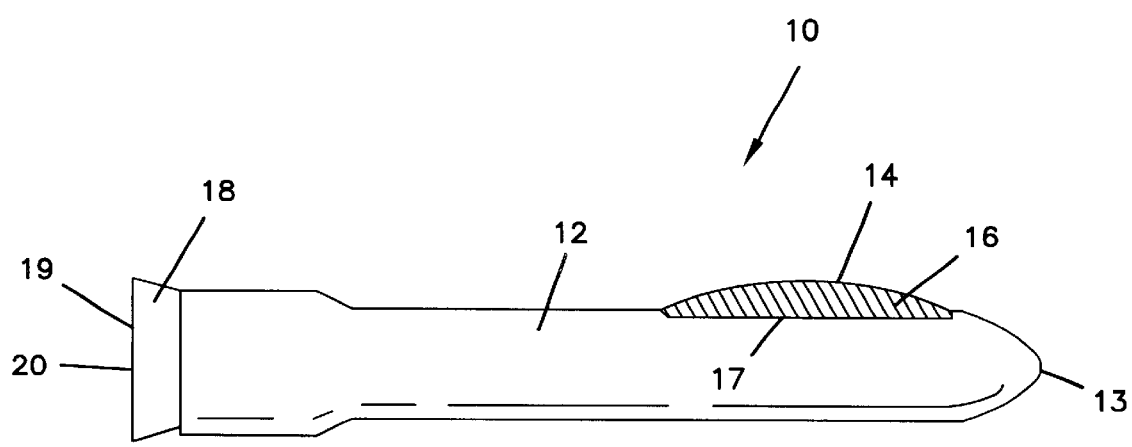
FIG. 1 is a side elevational view of an imaging instrument standoff device constructed and arranged in accordance with an embodiment of the invention.

FIG. 1 shows an expandable standoff device 10 constructed and arranged in accordance with an embodiment of the invention. Standoff device 10 includes an elongate substantially rigid cover 12 having a tip 13. An elastic sheath 14 is positioned within the cover 12, and an exposed portion 16 of the cover 12 extends through an opening 17 in the cover 12. A sealing ring 18 is optionally provided at the end 19 opposite the tip 13. Sealing ring 18 provides an opening 20 for receiving the probe of the imaging instrument (shown in FIG. 2), and forms a fluid tight seal between the various components of the standoff device 10.

Figure 2:
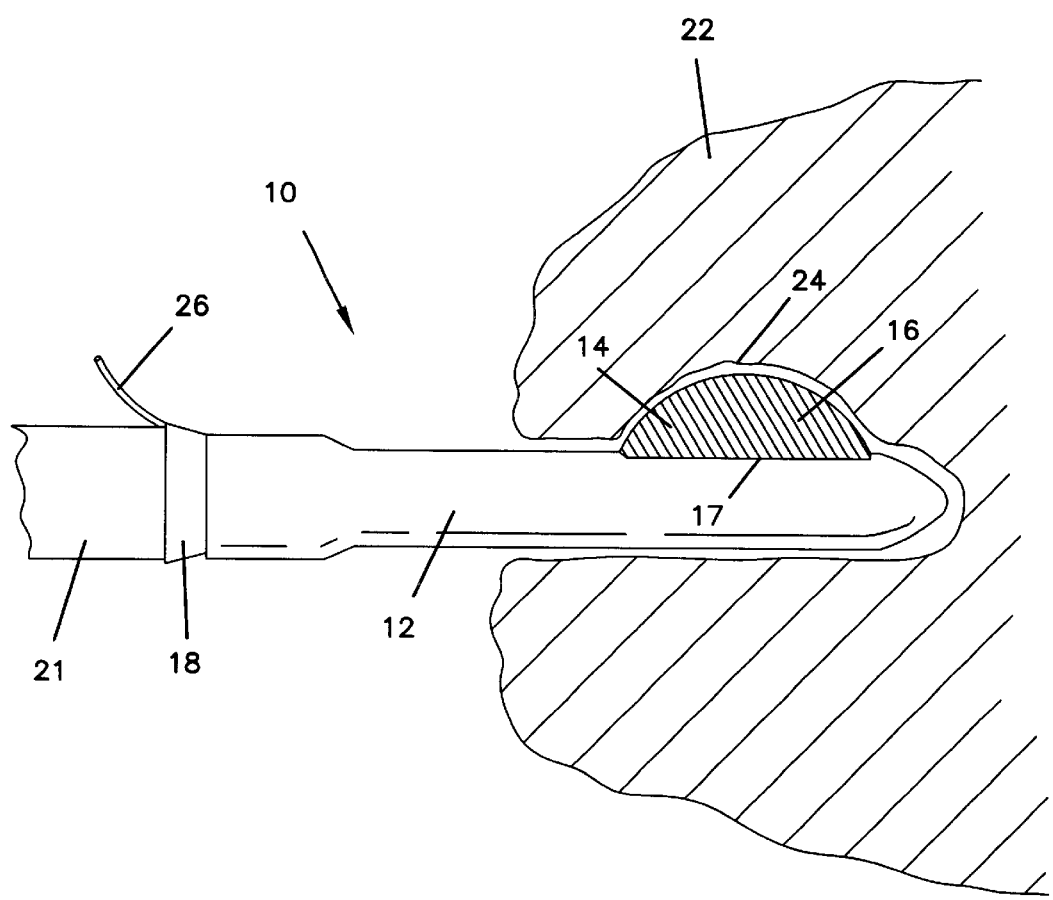
FIG. 2 is a side elevational view of an imaging instrument standoff device constructed and arranged in accordance with an embodiment of the invention, the standoff device in an expanded state and depicted in an endocavity of a patient.

In reference now to FIG. 2, the standoff device 10 is shown in use on an imaging instrument 21 placed within a stylized cross-section of a patient 22. In use, the exposed portion 16 of the standoff device 10 is expanded by fluid pressure to press against and adjust the tissue surface 24 of the patient 22. The fluid pressure is provided by a fluid source, such as a syringe (not shown), and is transmitted along conduit 26 into the interior of the standoff device 10. The substantially rigid cover 12 to the standoff device 10 contains the pressure within the standoff device, resulting in expansion of the sheath 14 primarily at exposed portion 16.

Depending upon the amount of pressure transmitted by the fluid, the size of the exposed portion 16 increases or decreases. By altering the pressure, the size of the exposed portion 16 is readily adjustable. Such adjustment is useful in moving the tissue surface 24 so as to maximize the quality of the image generated by the imaging instrument 21, and also allows slight adjustment of tissue within the patient. Such adjustments may be made by rotation of the imaging instrument and standoff device, as well as by increasing or decreasing the size of the exposed portion 16 of the elastic sheath 14.

The inventive standoff device 10 provides an increase in patient comfort by having a standoff portion that contracts. This contraction allows insertion of the probe of the imaging instrument 21 into an endocavity of a patient prior to expansion of the exposed portion 16, followed by expansion of the exposed portion 16 only during the imaging analysis. In this manner the standoff device 10 has a significantly reduced profile while being inserted and removed from the endocavity of the patient, yet can still perform well as a standoff.

Figure 3:
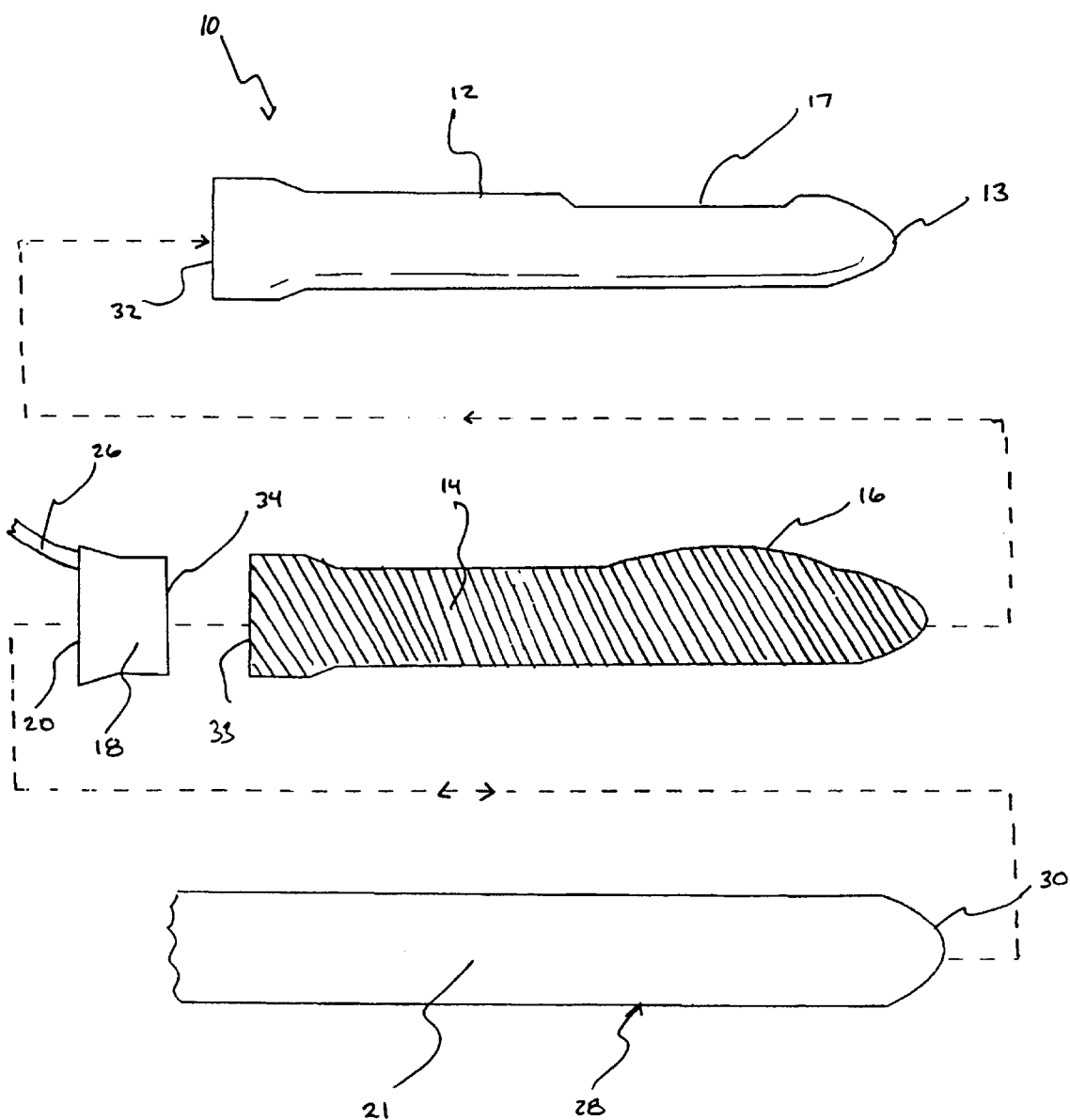
FIG. 3 is an exploded side elevational view of an imaging instrument standoff device constructed and arranged in accordance with an embodiment of the invention, showing the individual parts of the standoff device.

The various components of the standoff device 10 are shown in exploded view in FIG. 3. In the embodiment depicted in FIG. 3, the substantially rigid cover 12 includes an opening 17 from which the exposed portion 16 of the sheath 14 extends. Rigid cover 12 also includes an opening 32 opposite tip 13. Sheath 14 slides into the opening 32 of the rigid cover in order to place the exposed portion 16 of the sheath 14 in the opening 17 of the cover 12. Sheath 16 also includes an opening 33 opposite the tip 13, and opening 33 is configured to form a fluid-tight seal with the sealing ring 18. Sealing ring 18 is preferably hollow, with a first opening 34 and a second opening 20. Openings 34 and 20 provide a conduit through which the tip 30 of the probe 28 of the imaging instrument 21 may be inserted.

The various openings 32, 33, 34, 20 are preferably formed in such a manner that fluid tight seals are formed between the various components of the standoff device 12 and the imaging instrument 21. The most important seal is formed between the probe 28 and the sheath 14, because these two components combine to form the sealed volume into which the pressurized fluid is inserted to expand the exposed portion 16 of the sheath 14.

In the embodiment depicted, the elastic sheath 14 surrounds and substantially encapsulates the probe 28 of the imaging instrument 21. However, it will be appreciated that alternative embodiments are possible in which the sheath 14 is reduced in size while still providing an expandable elastic portion that provides standoff functionality. For example, the sheath 14 can be reduced to be substantially the same size as the opening 17 in the rigid cover 12 and be permanently fused to the rigid cover 18 around the edge of the opening 17. In said embodiment the sheath 14 and cover 12 become essentially one piece, although they are made of different materials.

Figure 4A:
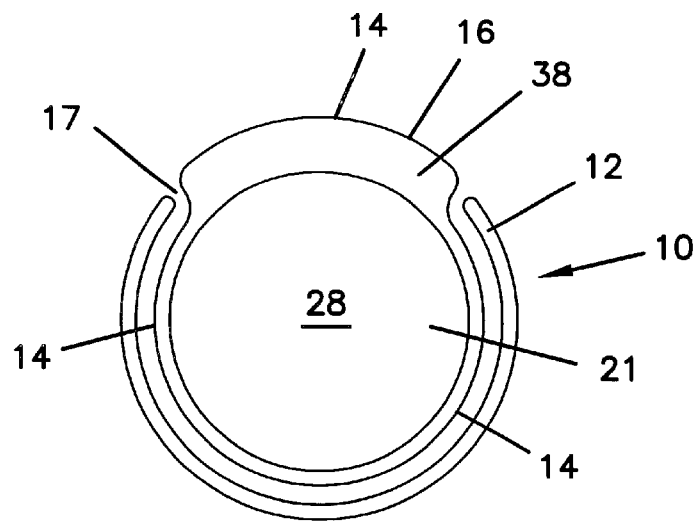
FIG. 4A is a cross sectional view of an imaging instrument standoff device constructed and arranged in accordance with an implementation of the invention, showing the standoff device in a contracted position.
Figure 4B:
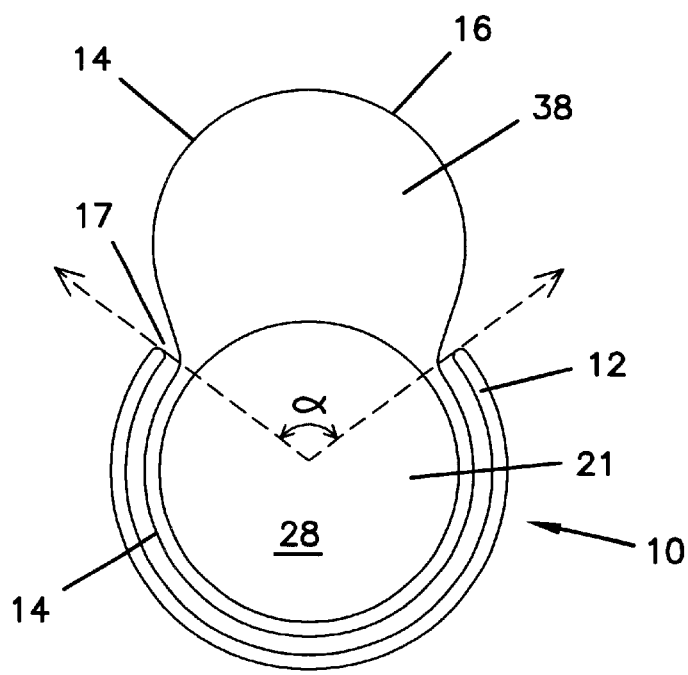
FIG. 4B is a cross sectional view of an imaging instrument standoff device constructed and arranged in accordance with an implementation of the invention, showing the standoff device in an expanded position.

In reference now to FIG. 4A and 4B, cross sectional representations of an imaging instrument 21 are depicted with a standoff device 10 shown in both a contracted position (FIG. 4A) and an expanded position (FIG. 4B). As shown in the embodiment depicted, the standoff device 10 includes a substantially rigid cover 12 that substantially surrounds the probe 28 of the imaging instrument 21. The exposed portion 16 of the sheath 14 is held within the interior of the cover 12 intermediate the cover 12 and the probe 28. The addition of fluid 38 into the space between the sheath 14 and the probe 28 results in expansion of the exposed portion 16. The substantially rigid cover 12 does not permit significant expansion along the remaining portions of the sheath 14.

The size of the opening 17 in the cover 14 may be expressed in various measurements, including total surface area; length and width; and arc. It will be appreciated that the surface area, length, and width of the opening 17 is likely to vary depending upon the size of the probe and the desired amount of extension achieved by exposed portion 16. Generally, larger probes 21 will require larger openings 17. However, in certain embodiments, even relatively large probes 21 may have small openings 17 if such openings provide a sufficient exposed portion 16 for accomplishing the standoff necessary for the medical procedures for which the probe will be used. In addition, another way of determining the size of the opening 17 is by the approximate arc in degrees of the opening 17, as measured from the approximate center of the probe 28. This arc, identified as α in FIG. 4B, is preferably less than or equal to approximately 180 degrees, more preferably less than 120 degrees. In certain implementations, the arc α is 90 degrees or less.

The fluid used to expand the elastic sheath is preferably a liquid, and is preferably transparent to ultrasound. Water is a preferred liquid used to expand the elastic sheath, although other liquids are also suitable. Aqueous saline solutions are also appropriate for use as the expansion fluid. The liquid is preferably non-toxic to tissue in order to prevent injury to the patient in the unexpected event that a leak in the elastic sheath 14 develops. Also, although the fluid is preferably a liquid, it may also be a gas in certain implementations.

Suitable materials used for forming the elastic sheath include natural and synthetic latex rubber, as well as various elastomers suitable for contact with a patient. The elastomers are preferably hypoallergenic. Although the elastic sheath 14 is ideally disposed after use on each patient, it is alternatively sterilized between uses so that it can be used on more than one patient. In certain embodiments, the cover 12 is used to conduct imaging analysis on multiple patients, and is therefore constructed of a material suitable for sterilization, such as various plastic compositions. However, in alternative embodiments the cover 12 is used for only one medical procedure and is disposed after each use.

It will be appreciated that although the implementation of the invention described above is directed to an ultrasound probe, the present device may be used with other medical imaging modalities, and is not limited to ultrasound probes. In addition, while the present invention has been described with reference to several particular implementations, those skilled in the art will recognize that many changes may be made hereto without departing from the spirit and scope of the present invention.

I claim:

1. A directionally expandable standoff device for use with an imaging instrument, the standoff device comprising:
    an elastic sheath configured for placement over a probe of an imaging instrument; and
    a substantially rigid cover configured for placement over the elastic sheath, said cover having a distal end, a proximal end, and a sidewall between the distal end and the proximal end, wherein the sidewall has at least one opening exposing a portion of the elastic sheath contained within the cover.

2. The directionally expandable standoff device according to claim 1, wherein the exposed portion of the elastic sheath is configured to expand through the opening in the cover upon insertion of a fluid into the elastic sheath.

3. The directionally expandable standoff device according to claim 2, wherein expansion is along a substantially orthogonal axis of the sidewall of the cover.

4. The directionally expandable standoff device according to claim 2, further comprising a conduit in fluid communication with the elastic sheath, the conduit configured and arranged to provide fluid to expand the exposed portion of the elastic sheath.

5. The directionally expandable standoff device according to claim 4, wherein the conduit is flexible.

6. The directionally expandable standoff device according to claim 2, wherein the exposed portion of the elastic sheath is configured to expand through the opening in the cover upon insertion of fluid into the elastic sheath.

7. The directionally expandable standoff device according to claim 1, wherein the exposed portion of the elastic sheath is configured and arranged such that it has an unexpanded state substantially flush with the cover.

8. The directionally expandable standoff device according to claim 1, wherein the exposed portion of the elastic sheath is confined to an arc of less than or equal to 180 degrees around the approximate center of the substantially rigid cover.

9. The directionally expandable standoff device according to claim 1, wherein the exposed portion of the elastic sheath is confined to an arc of less than or equal to 90 degrees around the approximate center of the substantially rigid cover.

10. The directionally expandable standoff device according to claim 1, further comprising a sealing ring configured and arranged to create a substantially fluid-tight seal between the elastic sheath and the probe of the imaging instrument.

11. The directionally expandable standoff device according to claim 1, wherein the sheath is latex.

12. The directionally expandable standoff device according to claim 1, wherein the elastic sheath is configured and arranged to be repeatedly expanded and contracted.

13. The directionally expandable standoff device according to claim 1, wherein the elastic sheath is configured for placement over an ultrasound probe.

14. A directionally expandable standoff device for use with an imaging instrument, the standoff device comprising:
    an elastic sheath configured for placement over the probe of an imaging instrument; and
    a substantially rigid cover configured for placement over the elastic sheath, said cover having a distal end, a proximal end, and a sidewall between the distal end and the proximal end, wherein the sidewall has at least one opening exposing a portion of the elastic sheath contained within the cover, the exposed portion of the elastic sheath confined to an arc of less than or equal to 180 degrees around the approximate center of the substantially rigid cover.

15. The directionally expandable standoff device according to claim 14, wherein the exposed portion of the elastic sheath is configured and arranged such that it has an unexpanded state substantially flush with the cover and an expanded state wherein a portion of the elastic sheath is more than 0.5 inches from the cover when in the unexpanded state.

16. The directionally expandable standoff device according to claim 14, further comprising a conduit in fluid communication with the elastic sheath configured and arranged to provide the fluid to expand the exposed portion of the elastic sheath.

17. A method of examining a patient using an imaging instrument, the method comprising:
    providing an imaging instrument; and
    providing a directionally expandable standoff device for use with an imaging instrument, the standoff device comprising an elastic sheath configured for placement over the probe of an imaging instrument; and a substantially rigid cover configured for placement over the expandable sheath, said cover having a distal end, a proximal end, and a sidewall between the distal end and the proximal end, wherein the sidewall has at least one opening exposing a portion of the elastic sheath contained within the cover; and
    expanding the directionally expandable standoff device so as to position the imaging instrument relative to tissue of a patient.

18. The method according to claim 17, wherein the exposed portion of the elastic sheath is confined to an arc of less than or equal to 180 degrees around the approximate center of the imaging instrument.

19. The method according to claim 17, wherein the exposed portion of the elastic sheath is configured and arranged such that it has an unexpanded state substantially flush with the cover and an expanded state wherein a portion of the elastic sheath is more than 0.5 inches from the sheath when in the unexpanded state.

* * * * *